(12) United States Patent
Ding

(10) Patent No.: US 6,763,267 B2
(45) Date of Patent: *Jul. 13, 2004

(54) VENTRICULAR CONDUCTION DELAY TRENDING SYSTEM AND METHOD

(75) Inventor: Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 46 days.

This patent is subject to a terminal disclaimer.

(21) Appl. No.: 10/054,427

(22) Filed: Jan. 22, 2002

(65) Prior Publication Data

US 2002/0062139 A1 May 23, 2002

Related U.S. Application Data

(63) Continuation of application No. 09/615,588, filed on Jul. 13, 2000.

(51) Int. Cl.[7] .............................................. A61N 1/368
(52) U.S. Cl. ........................................................ 607/9
(58) Field of Search ............................... 607/9, 25, 27; 600/516, 510, 509

(56) References Cited

U.S. PATENT DOCUMENTS

| | | | |
|---|---|---|---|
| 4,059,116 A | 11/1977 | Adams | 128/419 PG |
| 4,163,451 A | 8/1979 | Lesnick et al. | 128/419 PG |
| 4,208,008 A | 6/1980 | Smith | 371/15 |
| RE30,387 E | 8/1980 | Denniston III, et al. | 128/419 |
| 4,432,360 A | 2/1984 | Mumford et al. | 128/419 PG |
| 4,503,857 A | 3/1985 | Boute et al. | 128/419 PG |
| 4,562,841 A | 1/1986 | Brockway et al. | 128/419 PG |
| 4,596,255 A | 6/1986 | Snell et al. | 128/697 |
| 4,791,936 A | 12/1988 | Snell et al. | 128/697 |
| 4,809,697 A | 3/1989 | Causey, III et al. | 128/419 PT |
| 4,830,006 A | 5/1989 | Haluska et al. | 607/4 |

(List continued on next page.)

FOREIGN PATENT DOCUMENTS

| | | | |
|---|---|---|---|
| EP | 0033418 | 12/1980 | ............ A61N/1/36 |
| EP | 0360412 | 3/1990 | .......... A61N/1/365 |
| EP | 0401962 | 12/1990 | .......... A61N/1/368 |
| EP | 0597459 | 5/1994 | ............ A61N/1/39 |
| EP | 0617980 | 10/1994 | .......... A61N/1/368 |
| EP | 0748638 | 12/1996 | .......... A61N/1/368 |
| WO | WO-93/02746 | 2/1993 | .......... A61N/1/368 |
| WO | 95/09029 | 4/1995 | |
| WO | WO-97/11745 | 4/1997 | .......... A61N/1/362 |
| WO | WO-98/48891 | 11/1998 | .......... A61N/1/362 |
| WO | WO-00/71200 | 11/2000 | .......... A61N/1/362 |
| WO | WO-0071202 | 11/2000 | .......... A61N/1/362 |
| WO | WO-00/71203 | 11/2000 | ............ A61N/1/39 |

OTHER PUBLICATIONS

Mehra, R. et al., "Prevention of Atrial Fibrillation/Flutter by Pacing Techniques", *Interventional Electrophysiology, Second Edition*, Chapter 34, Futura Publishing Company, Inc., (1996), pp. 521–540.

(List continued on next page.)

*Primary Examiner*—Scott M. Getzow
(74) *Attorney, Agent, or Firm*—Schwegman, Lundberg, Woessner & Kluth, P.A.

(57) ABSTRACT

A method and system for ascertaining the condition of the heart's conduction system in a patient treated for congestive heart failure with pacing therapy. In accordance with the invention, changes in ventricular activation patterns are monitored over time in order to detect changes in the heart's conduction system that may occur due to physiological regeneration of conduction pathways. The activation patterns are reflected by electrogram signals detected from different ventricular locations. By measuring the difference in conduction times of an excitation impulse traveling from the AV node to the different ventricular locations, a parameter representative of the heart's conduction system is obtained that may be used to adjust the pacing therapy in accordance therewith.

20 Claims, 3 Drawing Sheets

U.S. PATENT DOCUMENTS

| | | | |
|---|---|---|---|
| 4,869,252 A | 9/1989 | Gilli | 128/419 PG |
| 4,890,617 A | 1/1990 | Markowitz et al. | 128/419 PG |
| 4,905,697 A | 3/1990 | Heggs et al. | 128/419 PG |
| 4,920,965 A | 5/1990 | Funke et al. | 128/419 PG |
| 4,940,054 A | 7/1990 | Grevis et al. | 128/419 PG |
| 4,941,471 A | 7/1990 | Mehra | 128/419 |
| 4,944,298 A | 7/1990 | Sholder | 128/419 PG |
| 4,944,928 A | 7/1990 | Grill et al. | 423/161 |
| 4,945,909 A | 8/1990 | Fearnot et al. | 128/419 PG |
| 4,972,834 A | 11/1990 | Begemann et al. | 128/419 |
| 4,998,974 A | 3/1991 | Aker | 128/419 PG |
| 5,012,814 A | 5/1991 | Mills et al. | 128/691 |
| 5,042,480 A | 8/1991 | Hedin et al. | 128/419 PG |
| 5,085,215 A | 2/1992 | Nappholz et al. | 128/419 PG |
| 5,101,824 A | 4/1992 | Lekholm | 128/419 PG |
| 5,107,850 A | 4/1992 | Olive | 128/705 |
| 5,127,404 A | 7/1992 | Wyborny et al. | 128/419 P |
| 5,129,394 A | 7/1992 | Mehra | 128/419 PG |
| 5,139,020 A | 8/1992 | Koestner et al. | 128/419 PG |
| 5,144,949 A | 9/1992 | Olson | 128/419 |
| 5,156,147 A | 10/1992 | Warren et al. | 128/419 PG |
| 5,156,154 A | 10/1992 | Valenta, Jr. et al. | 128/661.09 |
| 5,179,949 A | 1/1993 | Chirife | 128/419 PG |
| 5,183,040 A | 2/1993 | Nappholz et al. | 128/419 PG |
| 5,184,614 A | 2/1993 | Collins et al. | 128/419 PG |
| 5,188,106 A | 2/1993 | Nappholz et al. | 128/419 PG |
| 5,193,535 A | 3/1993 | Bardy et al. | 128/419 D |
| 5,193,550 A | 3/1993 | Duffin | 129/697 |
| 5,197,467 A | 3/1993 | Steinhaus et al. | 128/419 PG |
| 5,207,219 A | 5/1993 | Adams et al. | 128/419 D |
| 5,282,836 A | 2/1994 | Kreyenhagen et al. | 607/4 |
| 5,284,491 A | 2/1994 | Sutton et al. | 607/17 |
| 5,292,339 A | 3/1994 | Stephens et al. | 607/15 |
| 5,292,341 A | 3/1994 | Snell | 607/30 |
| 5,311,874 A | 5/1994 | Baumann et al. | 128/705 |
| 5,312,452 A | 5/1994 | Salo | 607/17 |
| 5,331,966 A | 7/1994 | Ziehm | 128/696 |
| 5,334,220 A | 8/1994 | Sholder | 607/9 |
| 5,350,409 A | 9/1994 | Stoop et al. | 607/17 |
| 5,356,425 A | 10/1994 | Bardy et al. | 607/14 |
| 5,360,437 A | 11/1994 | Thompson | 607/30 |
| 5,365,932 A | 11/1994 | Greenhut | 128/696 |
| 5,372,607 A | 12/1994 | Stone et al. | 607/30 |
| 5,379,776 A | 1/1995 | Murphy et al. | 128/705 |
| 5,383,910 A | 1/1995 | den Dulk | 607/14 |
| 5,387,229 A | 2/1995 | Poore | 607/18 |
| 5,391,189 A | 2/1995 | van Krieken et al. | 607/17 |
| 5,395,373 A | 3/1995 | Ayers | 607/8 |
| 5,395,397 A | 3/1995 | Lindgren et al. | 607/9 |
| 5,400,796 A | 3/1995 | Wecke | 128/705 |
| 5,411,524 A | 5/1995 | Rahul | 607/4 |
| 5,411,531 A | 5/1995 | Hill et al. | 607/14 |
| 5,417,714 A | 5/1995 | Levine et al. | 607/9 |
| 5,423,869 A | 6/1995 | Poore et al. | 607/18 |
| 5,431,691 A | 7/1995 | Snell et al. | 607/27 |
| 5,437,285 A | 8/1995 | Verrier et al. | 128/702 |
| 5,462,060 A | 10/1995 | Jacobson et al. | 128/702 |
| 5,474,574 A | 12/1995 | Payne et al. | 607/7 |
| 5,480,413 A | 1/1996 | Greenhut et al. | 607/14 |
| 5,486,198 A | 1/1996 | Ayers et al. | 607/5 |
| 5,487,752 A | 1/1996 | Salo et al. | 607/17 |
| 5,507,782 A | 4/1996 | Kieval et al. | 607/9 |
| 5,507,784 A | 4/1996 | Hill et al. | 607/14 |
| 5,514,163 A | 5/1996 | Markowitz et al. | 607/4 |
| 5,522,850 A | 6/1996 | Yomtov et al. | 607/5 |
| 5,522,859 A | 6/1996 | Stroebel et al. | 607/19 |
| 5,523,942 A | 6/1996 | Tyler et al. | 364/401 |
| 5,527,347 A | 6/1996 | Shelton et al. | 607/9 |
| 5,534,016 A | 7/1996 | Boute | 607/9 |
| 5,540,232 A | 7/1996 | Laney et al. | 128/697 |
| 5,540,727 A | 7/1996 | Tockman et al. | 607/18 |
| 5,545,182 A | 8/1996 | Stotts et al. | 607/5 |
| 5,545,186 A | 8/1996 | Olson et al. | 607/14 |
| 5,549,649 A | 8/1996 | Florio et al. | 607/15 |
| 5,549,654 A | 8/1996 | Powell | 607/32 |
| 5,554,174 A | 9/1996 | Causey, III | 607/5 |
| 5,560,369 A | 10/1996 | McClure et al. | 128/704 |
| 5,560,370 A | 10/1996 | Verrier et al. | 128/705 |
| 5,584,864 A | 12/1996 | White | 607/5 |
| 5,584,867 A | 12/1996 | Limousin et al. | 607/9 |
| 5,591,215 A | 1/1997 | Greenhut et al. | 607/14 |
| 5,605,159 A | 2/1997 | Smith et al. | 128/702 |
| 5,607,460 A | 3/1997 | Kroll et al. | 607/30 |
| 5,613,495 A | 3/1997 | Mills et al. | 128/696 |
| 5,620,471 A | 4/1997 | Duncan | 607/14 |
| 5,620,473 A | 4/1997 | Poore | 607/27 |
| 5,622,178 A | 4/1997 | Gilham | 128/696 |
| 5,626,620 A | 5/1997 | Kieval et al. | 607/9 |
| 5,626,622 A | 5/1997 | Cooper | 607/18 |
| 5,626,623 A | 5/1997 | Kieval et al. | 607/23 |
| 5,632,267 A | 5/1997 | Hognelid et al. | 607/5 |
| 5,674,250 A | 10/1997 | de Coriolis et al. | 607/7 |
| 5,674,251 A | 10/1997 | Combs et al. | 607/4 |
| 5,674,255 A | 10/1997 | Walmsley et al. | 607/14 |
| 5,676,153 A | 10/1997 | Smith et al. | 128/702 |
| 5,683,429 A | 11/1997 | Mehra | 602/14 |
| 5,690,689 A | 11/1997 | Sholder | 607/24 |
| 5,700,283 A | 12/1997 | Salo | 607/17 |
| 5,713,929 A | 2/1998 | Hess et al. | 607/14 |
| 5,713,930 A | 2/1998 | van der Veen et al. | 607/25 |
| 5,713,932 A | 2/1998 | Gillberg et al. | 607/27 |
| 5,716,382 A | 2/1998 | Snell | 607/30 |
| 5,716,383 A | 2/1998 | Kieval et al. | 607/9 |
| 5,716,384 A | 2/1998 | Snell | 607/30 |
| 5,718,235 A | 2/1998 | Golosarsky et al. | 128/708 |
| 5,724,985 A | 3/1998 | Snell et al. | 128/697 |
| 5,725,559 A | 3/1998 | Alt et al. | 607/5 |
| 5,725,561 A | 3/1998 | Stroebel et al. | 607/9 |
| 5,730,141 A | 3/1998 | Fain et al. | 128/705 |
| 5,730,142 A | 3/1998 | Sun et al. | 128/705 |
| 5,738,096 A | 4/1998 | Ben-Haim | 128/653.1 |
| 5,741,304 A | 4/1998 | Patwardhan et al. | 607/5 |
| 5,741,308 A | 4/1998 | Sholder | 607/9 |
| 5,749,901 A | 5/1998 | Bush et al. | 607/5 |
| 5,749,906 A | 5/1998 | Kieval et al. | 607/9 |
| 5,755,736 A | 5/1998 | Gillberg et al. | 607/4 |
| 5,755,737 A | 5/1998 | Prieve et al. | 607/4 |
| 5,755,739 A | 5/1998 | Sun et al. | 607/14 |
| 5,755,740 A | 5/1998 | Nappholz | 607/18 |
| 5,759,196 A | 6/1998 | Hess et al. | 607/14 |
| 5,776,164 A | 7/1998 | Ripart | 607/5 |
| 5,776,167 A | 7/1998 | Levine et al. | 607/9 |
| 5,782,887 A | 7/1998 | van Krieken et al. | 607/25 |
| 5,788,717 A | 8/1998 | Mann et al. | 607/14 |
| 5,792,193 A | 8/1998 | Stoop | 607/14 |
| 5,800,464 A | 9/1998 | Kieval | 607/9 |
| 5,800,471 A | 9/1998 | Baumann | 607/25 |
| 5,814,077 A | 9/1998 | Sholder et al. | 607/9 |
| 5,814,081 A | 9/1998 | Ayers et al. | 607/5 |
| 5,814,085 A | 9/1998 | Hill | 607/14 |
| 5,836,975 A | 11/1998 | DeGroot | 607/5 |
| 5,836,987 A | 11/1998 | Baumann et al. | 607/17 |
| 5,840,079 A | 11/1998 | Warman et al. | 607/4 |
| 5,842,997 A | 12/1998 | Verrier et al. | 600/518 |
| 5,846,263 A | 12/1998 | Peterson et al. | 607/14 |
| 5,853,426 A | 12/1998 | Shieh | 607/5 |
| 5,855,593 A | 1/1999 | Olson et al. | 607/9 |
| 5,861,007 A | 1/1999 | Hess et al. | 607/9 |
| 5,865,838 A | 2/1999 | Obel et al. | 607/5 |
| 5,873,895 A | 2/1999 | Sholder et al. | 607/9 |
| 5,873,897 A | 2/1999 | Armstrong et al. | 607/14 |

| | | | |
|---|---|---|---|
| 5,891,178 A | 4/1999 | Mann et al. | 607/27 |
| 5,893,882 A | 4/1999 | Peterson et al. | 607/14 |
| 5,897,575 A | 4/1999 | Wickham | 607/4 |
| 5,902,324 A | 5/1999 | Thompson et al. | 607/9 |
| 5,928,271 A | 7/1999 | Hess et al. | 607/14 |
| 5,931,857 A | 8/1999 | Prieve et al. | 607/14 |
| 5,935,081 A | 8/1999 | Kadhiresan | 600/513 |
| 5,944,744 A | 8/1999 | Paul et al. | 607/9 |
| 5,951,592 A | 9/1999 | Murphy | 607/4 |
| 5,968,079 A | 10/1999 | Warman et al. | 607/5 |
| 5,974,341 A | 10/1999 | Er et al. | 607/31 |
| 5,978,710 A | 11/1999 | Prutchi et al. | 607/17 |
| 5,983,138 A | 11/1999 | Kramer | 607/9 |
| 5,987,354 A | 11/1999 | Cooper et al. | 607/5 |
| 5,987,356 A | 11/1999 | DeGroot | 607/5 |
| 5,991,656 A | 11/1999 | Olson et al. | 607/4 |
| 5,991,657 A | 11/1999 | Kim | 607/5 |
| 5,991,662 A | 11/1999 | Kim et al. | 607/27 |
| 5,999,850 A | 12/1999 | Dawson et al. | 607/4 |
| 6,026,320 A | 2/2000 | Carlson et al. | 600/510 |
| 6,041,251 A | 3/2000 | Kim et al. | 600/518 |
| 6,044,298 A | 3/2000 | Salo et al. | 607/17 |
| 6,047,210 A | 4/2000 | Kim et al. | 607/4 |
| 6,049,735 A | 4/2000 | Hartley et al. | 607/9 |
| 6,052,617 A | 4/2000 | Kim | 600/518 |
| 6,052,620 A | 4/2000 | Gillberg et al. | 607/4 |
| 6,058,328 A | 5/2000 | Levine et al. | 607/14 |
| 6,085,116 A | 5/2000 | Hiscock et al. | 607/5 |
| 6,081,745 A | 6/2000 | Mehra | 607/4 |
| 6,081,746 A | 6/2000 | Pendekanti et al. | 607/5 |
| 6,081,747 A | 6/2000 | Levine et al. | 607/9 |
| 6,081,748 A | 6/2000 | Struble et al. | 607/9 |
| RE36,765 E | 7/2000 | Mehra | 607/4 |
| 6,088,618 A | 7/2000 | Kerver | 607/30 |
| 6,122,545 A | 9/2000 | Struble et al. | 607/9 |
| 6,128,529 A | 10/2000 | Esler | 607/4 |
| 6,129,745 A | 10/2000 | Sun et al. | 607/27 |
| 6,223,072 B1 | 4/2001 | Mika et al. | 600/510 |
| 6,249,699 B1 | 6/2001 | Kim | 607/4 |
| 6,256,534 B1 | 7/2001 | Dahl | 607/5 |
| 6,263,242 B1 | 7/2001 | Mika et al. | 607/9 |
| 6,266,554 B1 | 7/2001 | Hsu et al. | 600/515 |
| 6,272,380 B1 | 8/2001 | Warman et al. | 607/5 |
| 6,285,907 B1 | 9/2001 | Kramer et al. | 607/9 |
| 6,353,759 B1 | 3/2002 | Hartley et al. | 607/9 |
| 6,353,761 B1 | 3/2002 | Conley et al. | 607/28 |
| 6,411,847 B1 | 6/2002 | Mower | 607/9 |
| 6,411,848 B2 | 6/2002 | Kramer et al. | 607/9 |
| 6,424,865 B1 | 7/2002 | Ding | 607/9 |
| 6,430,438 B1 | 8/2002 | Chen et al. | 607/5 |
| 6,438,410 B2 | 8/2002 | Hsu et al. | 600/516 |
| 6,501,987 B1 | 12/2002 | Lovett et al. | 607/9 |
| 6,501,988 B2 | 12/2002 | Kramer et al. | 607/9 |
| 6,512,951 B1 | 1/2003 | Marcovecchio et al. | 607/5 |
| RE38,119 E | 5/2003 | Mower | 607/9 |

OTHER PUBLICATIONS

Morris et al., "Intracardiac Electrogram Transformation: Morphometric Implications for Implantable Devices", *Journal of Electrocardiology*, 29 Supplement, (1996), pp. 124–129.

Mower, Morton, *U.S. Patent Office Patent Application Information Retrieval (PAIR) search results for U.S. Patent Application Ser. No. 10/214,474, filed on Aug. 8, 2002, entitled "Method and Apparatus for Treating Hemodynamic Disfunction"*, 3.

Murgatroyd, F.D. et al., "A New Pacing Algorithm for Overdrive Suppression of Atrial Fibrillation", *Pace, vol. 17.*, (Nov. 1994, Part), pp.1966–1973.

Schuller, et al., "Far Field R–Wave Sensing–An Old Problem Repeating", *PACE, 19, Part II*, NASPE Abstract No. 264, (1996), p. 631.

Seim, G. et al., "Classification of Atrial Flutter and Atrial Fibrillation Using an Atrial Dispersion Index (ADI)", *Guidant CRM Therapy Research Peer Review Report Revision 2.0*, (Jan. 6, 1999), 27 p.

Stephany et al., "Real–Time Estimation of Magnitude–Square Coherence for Use in Implantable Devices", *IEEE Computers in Cardiology*, (1992), pp. 375–378.

Sutton, R., "Pacing in Atrial Arrhythmias", *PACE, vol. 13*, (Dec. 1990, Part), pp. 1823–1827.

Swiryn, S., et al., "Detection of Atrial Fibrillation by Pacemakers and Antiarrhythmic Devices", *Nonpharmacological Management of Arial Fibrillation, Chapter 21*, Futura Publishing Co, Inc. Armonk, NY, (1997), pp. 309–318.

Zhu, D. W., "Electrophysiology, Pacing and Arrhythmia", *Clin. Cardiol., vol. 19*, (Sep. 1996), pp. 737–742.

*Metrix Model 3020 Implantable Atrial Defibrillator*, Physician's Manual, InControl, Inc., Redmond, WA, (1998), pp. 4–24 –4–27.

"French CNH Equipment Approvals", *Clinica, 417, p. 9*, (Sep. 5, 1990), 3 pp.

Pacemaker System Guide for Pulsar Max II; Multiprogrammable

Pacemakers, Product brochure published by Guidant Corporation, (Apr. 18, 1999), pp. 6–48 and 6–49.

"Pacemaker System Guide for Pulsar Max II; Multiprogrammable Pacemakers", Product brochure published by Guidant Corporation, (1999), pp. 6–39 –6–51.

"Rate–Adaptive Devices Impact Pacemaker Market", *Clinica, 467, p. 16*, (Sep. 11, 1991), 6 pages.

"Vitatron Medical Harmony Automatic Dual Chamber Pacemaker Product Information and Programming Guide", Product Brochure published by Vitatron Medical, (Date Unknown), 22 pages.

Ayers, Gregory M., et al., "Ventricular Proarrhythmic Effects of Ventricular Cycle Length and Shock Strength in a Sheep Model of Transvenous Atrial Defibrillation", *Circulation, 89 (1)*, (Jan. 1994), pp. 413–422.

Blommaert, D., et al., "Effective Prevention of Atrial Fibrillation by Continuous Atrial Overdrive Pacing After Artery Bypass SAurgery", *JACC. vol. 35, No. 6*, (May 2000), pp. 1411–1415.

Campbell, R. M. et al., "Atrial Overdrive Pacing for Conversion of Atrial Flutter in Children", *Pediatrics, vol. 75, No. 4*, (Arp. 1985), pp. 730–736.

Duckers, H. J. et al., "Effective use of a novel rate–smoothing algorithm in atrial fibrillation by ventricular pacing", *European Heart Journal, 18*, (1997), pp. 1951–1955.

Fahy, G. J. et al., "Pacing Strategies to Prevent Atrial Fibrillation", *Atrial Fibrillation, 14 (4)*, (Nov. 1996), pp. 591–596.

Fromer, M., et al., "Algorithm for the Prevention of Ventricular Tachycardia Onset: The Prevent Study", *The American Journal of Cardiology, 83 (5B)*, (Mar. 11, 1999),pp. 45D–47D.

Garrigue, S., et al., "Prevention of Atrial Arrhythmias during DDD Pacing by Atrial Overdrive", *PACE, vol. 21*, (Sep. 1998), pp. 1751–1759.

Heuer, H., et al., "Dynamic Dual–Chamber Overdrive Pacing with an Implantable Pacemaker System: A New Method for Terminating Slow Ventricular Tachycardia", *Zeitschrift fur Kardiologie, 75*, German Translation by the Ralph McElroy Translation Company, Austin, TX, (1986), 5 p.

Heuer, H. et al., "Dynamische Zweikammer–Overdrive–Stimulation mit einem implantierbaren Schrittmachersystem als neue Methode zur Beendigung Langsamer ventrikularer Tachykardien", *Z Kardiol; 75*, Includes English translation (5 pp.),(1986), pp. 673–675.

Jenkins, et al., "Diagnosis of Atrial Fibrillation Using Electrogram from Chronic Leads: Evaluation of Computer Algorithm", *PACE, 11*, (1998), pp. 622–631.

Jung, J., et al., "Discrimination of Sinus Rhythm, Atrial Flutter, and Atrial Fibrillation Using Bipolar Endocardial Signals", *Journal of Cardiovascular Electrophysiology, 9 (7)*, (Jul. 1998), pp. 689–695.

VENTRICULAR CONDUCTION DELAY TRENDING SYSTEM AND METHOD

CROSS-REFERENCE TO RELATED APPLICATIONS

This patent application is a continuation of U.S. application Ser. No. 09/615,588, filed on Jul. 13, 2000, the specification of which is incorporated by reference herein.

FIELD OF THE INVENTION

This invention pertains to cardiac pacemakers and methods for operating such devices. In particular, the invention relates to a method and system for monitoring changes in a physiological condition of a patient treated for congestive heart failure with a pacemaker.

BACKGROUND

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. The most common way of treating CHF is drug therapy, but recent studies have demonstrated that some CHF patients may benefit from cardiac pacing therapy. Some CHF patients suffer from bradycardia, a traditional indication for cardiac pacing, but others exhibit a delay in ventricular contraction which leads to inadequate filling during diastole and decreased cardiac output. Such ventricular contraction delays can be due to some degree of AV block, and cardiac output in those patients can be improved by synchronizing atrial and ventricular contractions with dual-chamber pacing using a short programmed AV delay time. It has also been shown that some CHF patients suffer from intraventricular conduction defects (a.k.a. bundle branch blocks) such that their cardiac outputs can be increased by improving the synchronization of ventricular contractions. Ventricular synchrony can be improved either by pacing one ventricle or providing pacing to both ventricles separately, termed biventricular pacing.

The normal rhythmic impulse of the heart is first generated in pacemaker tissue known as the sino-atrial (SA) node, spreads throughout the atria causing atrial contraction, and is then conducted to the atrioventricular (AV) node where the impulse is delayed before passing into the ventricles. The ventricles of a normal heart are then electrically stimulated by excitation emanating from the AV node that spreads to the heart via specialized conduction pathways known as Purkinje fibers. The Purkinje system begins from the AV node as the bundle of His and then divides into right and left bundle branches to supply excitation to the right and left ventricles. The fibers lie beneath the endocardium and spread throughout each ventricular chamber where they penetrate into the myocardium and become continuous with the muscle fibers. The conduction velocity of the Purkinje fibers is very rapid so that the time between the impulse leaving the AV node and spreading to the entire endocardial surface of the ventricles is only approximately 0.03 seconds. Once the impulse has reached the ends of the Purkinje fibers, it is then transmitted through the ventricular muscle mass by the muscle fibers themselves with a conduction velocity only about one-sixth that of the Purkinje fibers. Because of the rapid excitation of the entire endocardial surface by the Purkinje system, however, the spread of excitation from the endocardial surface to the epicardial surface of the ventricles takes only about another 0.03 seconds. This means that in the normal heart, excitation of the first ventricular muscle fiber occurs only about 0.06 seconds before the last ventricular muscle fiber is excited. The result is a synchronous contraction in which all portions of the ventricular muscle in both ventricles begin contracting at nearly the same time.

Conventional cardiac pacing with implanted pacemakers involves electrical stimulation of the heart by an electrode in electrical contact with the myocardium. The pacemaker is usually implanted subcutaneously on the patient's chest, and is connected to an electrode for each paced heart chamber by leads threaded through the vessels of the upper venous system into the right heart and through the coronary sinus into the left heart. In response to sensed electrical cardiac events and elapsed time intervals, the pacemaker delivers to the myocardium a depolarizing voltage pulse of sufficient magnitude and duration to cause an action potential. A wave of depolarizing excitation then propagates through the myocardium, resulting in a heartbeat.

As noted above, some CHF patients suffer from defects of the Purkinje conduction system such as bundle branch block. Artificial ventricular pacing with an electrode fixed into an area of the myocardium does not use the heart's Purkinje conduction system because that system can only be entered by impulses emanating from the AV node. With pacing, the spread of excitation proceeds from the pacing electrode via the ventricular muscle fibers, thus bypassing the deficient conduction pathway in the CHF patient with bundle branch block and improving cardiac function. If the conduction system is normal or near-normal, however, such pacing can actually worsen cardiac function because the conduction velocity of muscle fibers is much less than that of Purkinje fibers. As pacing therapy continues in a CHF patient over time, a compensatory remodeling process can be expected to occur as the heart adapts to the benefit received from the chronic pacing. Such remodeling may partially regenerate the deficient conduction system. If such is the case, pacing therapy should be adjusted accordingly in order to maintain optimal cardiac function by, e.g., changing the AV delay time or possibly even discontinuing pacing. It would be advantageous in a CHF patient treated with pacing therapy, therefore, if changes in the condition of the heart's conduction system could be ascertained and monitored throughout the course of the therapy.

SUMMARY OF THE INVENTION

In accordance with the present invention, changes in the condition of the heart's conduction system are monitored by measuring changes in ventricular activation patterns as reflected by electrogram signals detected from different locations in the heart. In one embodiment, an atrial sensing channel detects electrogram signals from an atrial location, and ventricular sensing channels detect electrogram signals from first and second ventricular locations. Either after turning pacing off or during a heartbeat in which no ventricular pacing is delivered, ventricular depolarizations (i.e., R waves) are detected after detection of an atrial depolarization (i.e., a P wave). A PR interval is then calculated for each of the ventricular locations that represents the transit time for the excitation to travel through the conduction system and reach the ventricular electrode. A conduction delay time is then calculated as the difference between the two PR intervals that represents the difference in conduction times between the pathways to the first and second ventricular locations from the AV node. Changes in the conduction delay time are reflective of changes in the condition of the heart's conduction system and can thus be used to adjust pacing therapy for patient accordingly.

DESCRIPTION OF SPECIFIC EMBODIMENTS

Figure 1:
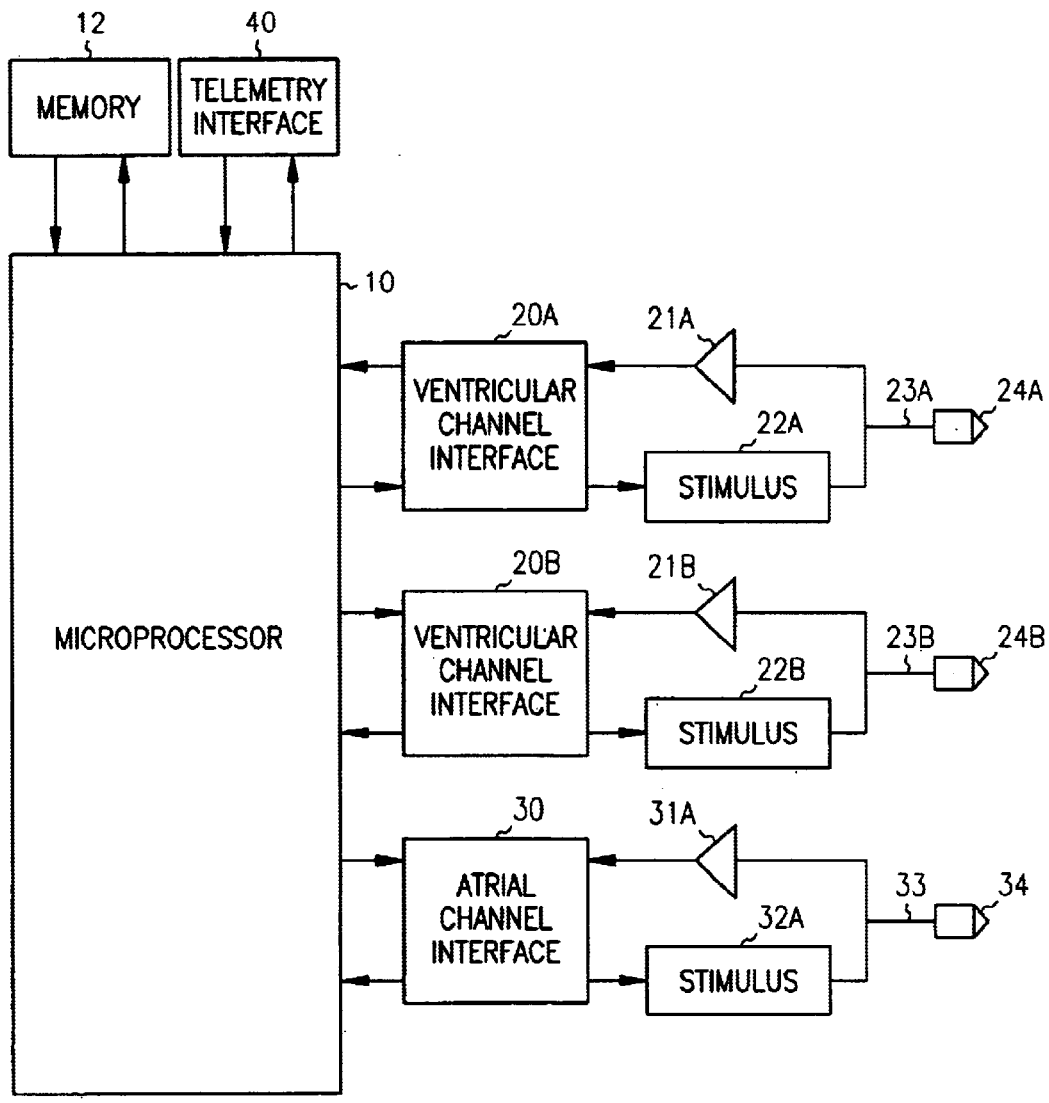
FIG. 1 is a system diagram of a pacemaker incorporating the present invention.

As noted above, cardiac pacing is beneficial to some CHF patients that suffer from conduction defects because excitation from a pacing pulse applied to a ventricle spreads without using the conduction system. Ventricular synchrony may thus be partially restored. The pacing modes most commonly used for treating CHF are DDD, DVI, and VDD. These are the ventricular pacing modes that also preserve atrioventricular coordination which is needed in CHF patients since diastolic filling (and hence cardiac output) is decreased without a well-coordinated contraction of the atria and ventricles. If the conduction system of the patient is found to be improving, however, it may be desirable to adjust the pacing therapy so that more advantage is taken of the patient's conduction system. Conversely, if the conduction system is deteriorating, the pacing therapy may be adjusted to, for example, increase the frequency of pacing or pace with a different AV interval.

In accordance with the invention, intrinsic electrograms are recorded from at least two ventricular electrodes at different locations during a brief period of no pacing, such as during clinical follow-up. The peak of the R wave from each electrogram is determined by a peak detection circuit or algorithm. The difference between the times of occurrence of these peaks (which can be measured with respect to a reference time, most conveniently the time of the preceding P wave) then represents the conduction delay, which is a parameter indicative of the condition of the patient's conduction system. The conduction delay may then be stored on a regular basis. The resulting data can then be analyzed manually or automatically in a periodic manner. A gradual decrease in the conduction delay suggests an improving conduction system, while a gradual increase in the conduction delay suggests further deterioration. Any sudden and sustained change in the conduction delay indicates either ectopic beats or electrode dislodgment. Thus, the conduction delay trending can also be used to monitor the relative position of the pacing/sensing leads.

Embodiments of the invention can be implemented into an implantable or external pacemaker as a diagnostic feature. Such a device records electrogram from at least two ventricular locations, preferably in the left ventricle. The conduction delays are measured in a manner as described above and stored in memory on a periodic basis. Data analysis can be done internally (i.e., by the pacemaker controller) or externally by an external programmer communicating with the pacemaker through a telemetry interface, with the results displayed by the programmer. Examples of such displayable results include trended conduction delays between selected regions, conduction delays in the form of means and standard deviations over the last period of data collection, slope of changes in the conduction delays over the last data collection period, warnings of a sudden change in the conduction delay value, prediction of future conduction delay values based upon past history, and notification if the conduction delays decrease or increase to a predetermined limit value. The time scale of the display may be made selectable between different time periods, such as weekly, monthly, or quarterly.

A pacemaker incorporating a particular embodiment of the invention will now be described. As used herein, the term pacemaker should be taken to mean any cardiac rhythm management device for pacing the heart and includes implantable pacemakers, external pacemakers, and implantable cardiac defibrillator/converters having a pacing functionality. A block diagram of a cardiac pacemaker having two ventricular pacing channels is shown in FIG. 1. The control unit of the pacemaker is made up of a microprocessor 10 communicating with a memory 12 via a bidirectional data bus 13, where the memory 12 typically comprises a ROM or RAM for program storage and a RAM for data storage. The control unit could also include dedicated circuitry either instead of, or in addition to, the programmed microprocessor for controlling the operation of the device. The pacemaker employs a programmable microprocessor to implement the logic and timing functions for operating the pacemaker in accordance with a specified pacing mode and pacing parameters as well as for performing the data acquisition functions of the invention. A telemetry interface 40 is also provided for communicating with an external programmer. Such an external programmer may be used to change the pacing mode, adjust operating parameters, receive data stored by the device, and issue commands that affect the operation of the pacemaker.

The pacemaker has atrial sensing/stimulation channels comprising electrode 34, lead 33, sensing amplifier/filter 31, pulse generator 32, and an atrial channel interface 30 which communicates bidirectionally with a port of microprocessor 10. The device also has two ventricular sensing/stimulation channels that include electrodes 24a–b, leads 23a–b, sensing amplifiers 21a–b, pulse generators 22a–b, and ventricular channel interfaces 20a–b where "a" designates one ventricular channel and "b" designates the other. For each channel, the same lead and electrode are used for both sensing (i.e., detecting P-waves and R-waves) and stimulation. The ventricular electrodes could be disposed in each of the ventricles for biventricular pacing or in only one ventricle for multi-site pacing of that ventricle. The channel interfaces 20a–b and 30 include analog-to-digital converters for digitizing sensing signal inputs from the sensing amplifiers and registers which can be written to by the microprocessor in order to output stimulation pulses, change the stimulation pulse amplitude, and adjust the gain and threshold values for the sensing amplifiers. After digitization of the sensed signals by the channel interfaces, the signal samples can be processed in the digital domain by algorithms executed by the microprocessor in order perform further filtering. The detection of R wave and P wave peaks for timing purposes can also be performed digitally. Alternatively, a standard peak detection circuit could be used.

Figure 2:
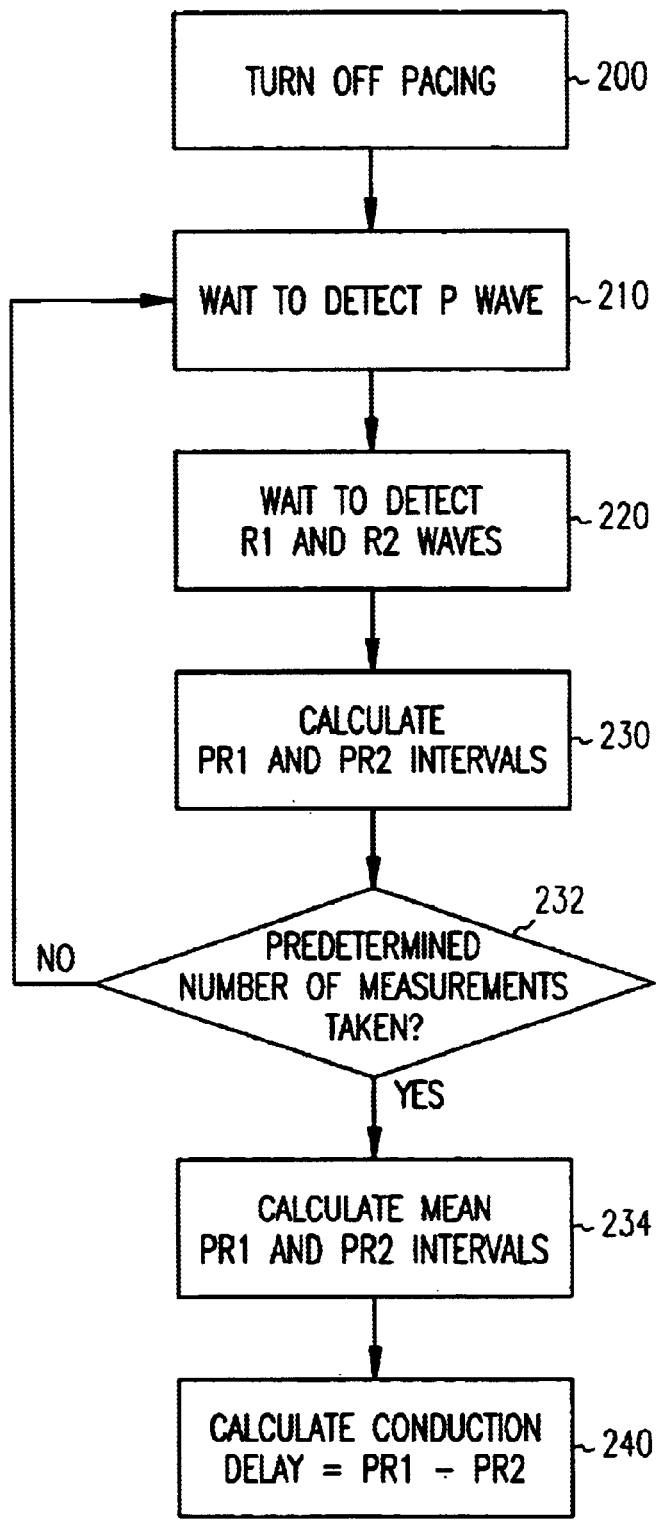
FIG. 2 shows the method steps for practicing the invention in which pacing is temporarily discontinued in order to measure the conduction delay time.

Shown in FIG. 2 is a flow chart detailing the steps performed by the controller 28 in accordance with a stored program in order to implement one form of the invention. In this embodiment, a conduction delay time is calculated upon an receipt of a command to do so, such as may be received from an external programmer. At step 200, pacing is discontinued in order to detect only intrinsic electrical activity transmitted by the heart's Purkinje conduction system. At step 210, a P wave is detected, and its time of occurrence is recorded. Subsequent R waves indicating ventricular depolarization are detected subsequently at step 220, with the R wave from the first ventricular sensing channel being designated R1, and the R wave from the second ventricular sensing channel designated R2. The respective times of occurrence of R1 and R2 are recorded. The time intervals PR1 and PR2 are then calculated at step 230 which represent the conduction time of the excitation impulse from the atrium to the first and second ventricular locations, respectively. At step 232, the controller determines whether the measurement has been performed on a predetermined number of cardiac cycles (beats). If not, then steps 210 to 230 are repeated to acquire PR1 and PR2 intervals from the next cycle. If the predetermined number of measurements have been obtained, then mean PR1 and PR2 values are calculated from the individual measurements at step 234. The conduction delay is then calculated as the difference between the mean interval values PR1 and PR2 at step 240. In other embodiments, ventricular depolarizations may be detected from further locations with additional conduction delays being calculated with respect thereto. Repeated measurements of the conduction delay over time enable the clinician to assess whether the patient's conduction system is improving, deteriorating, or remaining unchanged. The pacing therapy may then be adjusted accordingly. For example, if the patient's conduction system is improving as indicated by a decreasing conduction delay, it may be desirable in certain patients to increase the programmed AV interval in order to allow more heartbeats resulting from intrinsic excitation to occur.

Figure 3:
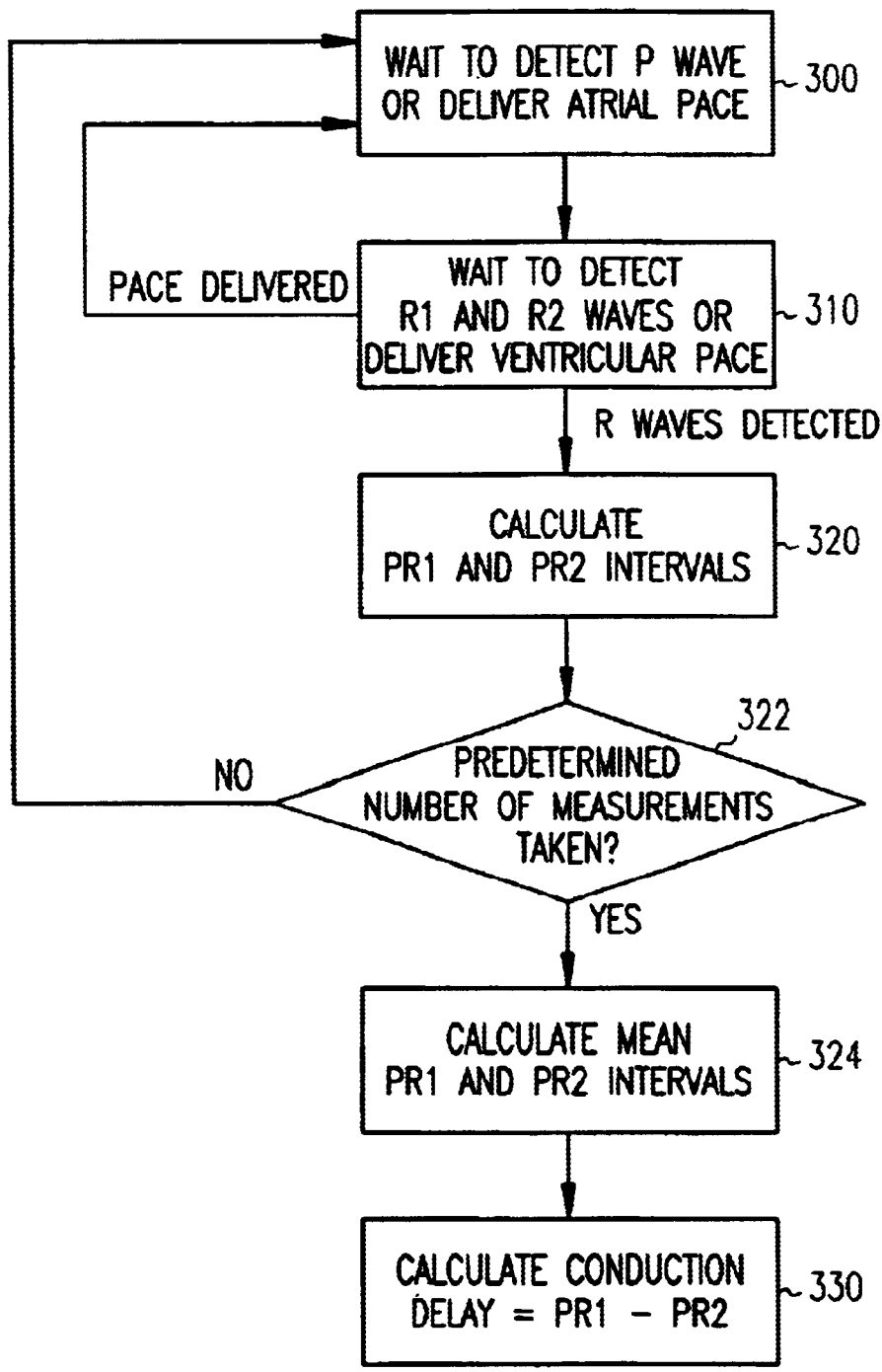
FIG. 3 shows the method steps for practicing the invention in which conduction delay times are periodically measured during periods of no ventricular pacing.

FIG. 3 shows a flowchart of the steps performed by the controller 28 in an embodiment of the invention in which conduction delays are measured automatically at specified times during heartbeats in which no ventricular pacing pulses are delivered. At step 300, either an atrial pace is delivered or a P wave is detected. In one embodiment, the method waits for a P wave and ignores atrial paces. In another embodiment, either an atrial pace or a P wave is used to measure the conduction delay, the atrial pace being considered equivalent to a P wave. The time of occurrence of the P wave (or atrial pace considered as a P wave) is then recorded, and the method waits for either a ventricular pace or R1 and R2 waves indicating ventricular depolarization at step 310. If a ventricular pace is delivered, the method returns to step 300 to wait for another P wave or atrial pace. If R1 and R2 waves are detected, their time of occurrence is recorded, and the PR1 and PR2 intervals are calculated at step 320. Steps 300 to 320 are repeated until a predetermined number of interval measurements have been taken, which is checked at step 322. At step 324, mean values of the PR1 and PR2 intervals are calculated from the predetermined number of individual measurements. The conduction delay is calculated as the difference between the mean PR1 and PR2 values at step 330. The calculated conduction delay may then be stored in a buffer that holds a history of such values. The contents of the buffer may then be downloaded to an external programmer for evaluation.

As noted above, measurement of conduction delays may be recorded and used by a clinician to adjust various pacing parameters. In another embodiment, pacing parameters are adjusted automatically by the microprocessor in accordance with the measured conduction delays. The parameter adjustment algorithm executed by the microprocessor may, for example, lengthen the programmed AV pacing interval by a predetermined amount in response to an increase in the average value (or other function) of a measured conduction delay over a specified time. Other pacing parameters could also be similarly automatically adjusted based upon the measurements.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising;

an atrial sensing channel for sensing electrical events occurring in an atrium;

first and second ventricular sensing channels for sensing electrical events occurring at first and second ventricular locations;

a ventricular pacing channel and a controller for pacing a ventricle in response to sensed events and lapsed time intervals in a mode such that the ventricle is paced at a programmed AV interval after an atrial sense or pace;

circuitry for detecting R waves in the ventricular sensing channels following detection of a P wave due to a detected atrial depolarization;

circuitry for measuring first and second PR intervals associated with the first and second ventricular sensing channels, and calculating a conduction delay value as the difference between the first and second PR intervals; and, wherein the controller is programmed to decrease or increase the programmed AV interval in accordance with an increase or decrease, respectively, of an average of conduction delays measured over a period of time.

2. The pacemaker of claim 1 further comprising circuitry for automatically measuring conduction delay values on a periodic basis and storing the values in memory.

3. The pacemaker of claim 1 further comprising an atrial pacing channel and wherein the detection circuitry waits for an intrinsic P wave for measurement of PR intervals.

4. The pacemaker of claim 3 wherein the controller is programmed to turn pacing off before measurement of PR intervals and calculation of conduction delays.

5. The pacemaker of claim 3 wherein the controller is programmed to measure PR intervals during atrial pacing.

6. The pacemaker of claim 5 wherein the controller is programmed to stop pacing before calculation of a conduction delay upon a command received from an external programmer.

7. The pacemaker of claim 1 further comprising an atrial pacing channel and wherein the detection circuitry detects delivery of an atrial pace and regards the time of occurrence of the pace as a P wave for purposes of measuring PR intervals.

8. The pacemaker of claim 1 further comprising a third ventricular sensing channel for sensing depolarizations at a third ventricular location and circuitry for measuring a PR interval and calculating conduction delay values with respect thereto.

9. The pacemaker of claim 1 wherein the controller is programmed to calculate and store conduction delays upon a command received from an external programmer.

10. The pacemaker of claim 1 wherein the controller is programmed to provide a warning if a conduction delay exceeds or falls below a specified limit value.

11. The pacemaker of claim 1 wherein the controller is programmed to provide a warning upon a sudden change in the calculated conduction delay.

12. The pacemaker of claim 1 wherein the controller is programmed to calculate a trend based upon past measurements of conduction delays.

13. The pacemaker of claim 1 wherein the controller is programmed to calculate conduction delays in the form of means and standard deviations over the last period of data collection.

14. The pacemaker of claim 1 wherein the controller is programmed to calculate a slope of changes in the conduction delays over the last data collection period.

15. The pacemaker of claim 1 wherein the controller is programmed to calculate a prediction of future conduction delay values based upon past history.

16. The pacemaker of claim 1 further comprising a second ventricular pacing channel and wherein the controller is programmed to deliver paces through the first and second pacing channels to two ventricular sites after the programmed AV interval following an atrial sense or pace.

17. The pacemaker of claim 16 further comprising an atrial pacing channel and wherein the detection circuitry waits for an intrinsic P wave for measurement of PR intervals.

18. The pacemaker of claim 17 wherein the controller is programmed to turn pacing off before measurement of PR intervals and calculation of conduction delays.

19. The pacemaker of claim 16 further comprising an atrial pacing channel and wherein the detection circuitry detects delivery of an atrial pace and regards the time of occurrence of the pace as a P wave for purposes of measuring PR intervals.

20. The pacemaker of claim 19 wherein the controller is programmed to measure PR intervals during atrial pacing.

* * * * *

UNITED STATES PATENT AND TRADEMARK OFFICE
CERTIFICATE OF CORRECTION

PATENT NO. : 6,763,267 B2
DATED : July 13, 2004
INVENTOR(S) : Ding

It is certified that error appears in the above-identified patent and that said Letters Patent is hereby corrected as shown below:

Title page,
Item [56], References Cited, FOREIGN PATENT DOCUMENTS, after "4/1995" insert -- A61N --.

Signed and Sealed this

Twenty-second Day of March, 2005

JON W. DUDAS
*Director of the United States Patent and Trademark Office*